United States Patent
Koski et al.

(10) Patent No.: US 11,802,834 B2
(45) Date of Patent: Oct. 31, 2023

(54) METHODS OF PREDICTING PROPERTIES OF A FEEDSTUFF SAMPLE

(71) Applicant: CAN TECHNOLOGIES, INC., Wayzata, MN (US)

(72) Inventors: Kelly Curran Koski, Crystal, MN (US); Gladys Ethel Margaria, Princeton, MN (US); Pam Paumen, Becker, MN (US); Kathryn L. Plaisance, Falcon Heights, MN (US); Vivian Adele Schouten, West Hills, CA (US); Guillermo Fernando Schroeder, Anoka, MN (US); Paul R. Score, Eden Prairie, MN (US); Yan Sun, Maple Grove, MN (US)

(73) Assignee: CAN TECHNOLOGIES, INC., Wayzata, MN (US)

( * ) Notice: Subject to any disclaimer, the term of this patent is extended or adjusted under 35 U.S.C. 154(b) by 177 days.

(21) Appl. No.: 17/452,520

(22) Filed: Oct. 27, 2021

(65) Prior Publication Data
US 2022/0128462 A1 Apr. 28, 2022

Related U.S. Application Data

(60) Provisional application No. 63/106,160, filed on Oct. 27, 2020.

(51) Int. Cl.
*G01N 21/3563* (2014.01)
*G01N 1/28* (2006.01)
(Continued)

(52) U.S. Cl.
CPC ......... *G01N 21/3563* (2013.01); *G01N 1/286* (2013.01); *G01N 1/44* (2013.01); *G01N 33/02* (2013.01); *G01N 2201/127* (2013.01)

(58) Field of Classification Search
CPC ...... G01N 21/3563; G01N 1/286; G01N 1/44; G01N 33/02; G01N 2201/127;
(Continued)

(56) References Cited

U.S. PATENT DOCUMENTS 6,008,053 A * 12/1999 Williams ............. G01N 21/359
426/2

OTHER PUBLICATIONS

Smadi et al., "Near infrared spectroscopy (NIRS) data analysis for a rapid and simultaneous prediction of feed nutritive parameters," Data In Brief, vol. 29, No. 105211, pp. 1-8. (Year: 2020).*
(Continued)

*Primary Examiner* — Kiho Kim

(57) ABSTRACT

Various embodiments disclosed relate to methods of predicting neutral detergent fiber digestibility (NDFD) properties of a feedstuff sample. A method of predicting neutral detergent fiber digestibility (NDFD) properties of a feedstuff sample includes collecting a near-infrared spectrum of the feedstuff sample to provide NIR data of the feedstuff sample. The method also includes predicting NDFD of the sample at an elapsed time, NDFD rate of the sample, and/or NDFD extent of the sample from the NIR data using a NIR/NDFD calibration model. Various embodiments provide a method of developing the NIR/NDFD calibration model using in vitro gas production (IVGP). Various embodiments provide a method of predicting digestibility of the feedstuff sample for an animal at a rumen passage rate (eNDF).

20 Claims, 4 Drawing Sheets

(51) Int. Cl.
*G01N 1/44* (2006.01)
*G01N 33/02* (2006.01)
(58) Field of Classification Search
CPC ..... G01N 2021/8466; G01N 2201/129; G01N 21/359; G01N 21/01; G01N 2021/0112; A23K 10/30; A23K 50/10
See application file for complete search history.

(56) References Cited

OTHER PUBLICATIONS

Goeser JP et al: "Modification of a rumen fluid priming technique for measuring in vitro neutral detergent fiber digestibility", Journal of Dairy Science, American Dairy Science Association, US, vol. 92, No. 8, 2009, pp. 3842-3848, XP026955583, ISSN: 0022-0302 [retrieved on Aug. 1, 2009].
Jung H G and Lamb J F S : "Stem Morphological and Cell Wall Traits Associated with Divergent In Vitro Neutral Detergent Fiber Digestibility in Alfalfa Clones", Crop Science, vol. 46, No. 5, 2006, pp. 2054-2061, XP055222548, DOI: 10.2135/cropsci2005.12.0470.

\* cited by examiner

METHODS OF PREDICTING PROPERTIES OF A FEEDSTUFF SAMPLE

CROSS-REFERENCE TO RELATED APPLICATIONS

This application claims the benefit of U.S. Provisional Application No. 63/106,160, filed Oct. 27, 2020, which is incorporated by reference herein in its entirety.

BACKGROUND

Forages are one of the main sources of nutrients for ruminants (e.g., cattle, sheep, goats) around the world as they are cheaper than other ingredients and provide many essential nutrients. Contrary to monogastric animals (e.g., pork, poultry), fiber contained in forages (measured as neutral detergent fiber (NDF)) is one of the main energy sources for ruminants because microbes in the rumen have the ability to ferment fiber fractions and produce energy for the ruminant animals. This is a biological process that is very dynamic and is one of the limiting steps in increasing productivity, health, and sustainability in milk and beef production. Thus, formulating optimal diets requires accurate and precise methods to measure the kinetics of digestibility of NDF in the rumen. The NDF digestibility is also referred to as NDFD, and has units of % NDF digestion at time t (e.g., % NDF disappearance at time t).

In situ methods of determining NDFD generally include adding ground samples to nylon bags in replicates and placing the bags into the rumen of cannulated animals. The bags are taken out of the rumen at different timepoints. By comparing the amount of NDF residue in the nylon bags and the NDF content of the original samples, the curve of NDFD versus time can be developed and can be used to calculate NDFD for a particular timepoint. This method requires rumen cannulated animals, a large amount of sample, is high in cost, gives highly variable results, and requires an extended period of time to complete (generally 25-30 days total).

The NDFD is typically determined in the lab (i.e., in vitro) by incubating forage samples with collected rumen fluid. The "Daisy Jar" method is one example of a technique for determining NDFD in the lab. Although lab methods to determine NDFD overcome some of the limitations of in situ methodology, they are still expensive, take a long time, may present safety risks, and are poorly correlated with in situ results.

SUMMARY OF THE INVENTION

The present invention provides a method of predicting neutral detergent fiber digestibility (NDFD) properties of a feedstuff sample. The method includes collecting a near-infrared (NIR) spectrum of the feedstuff sample to provide NIR data of the feedstuff sample. The method also includes predicting NDFD of the sample at an elapsed time, NDFD rate of the sample, and/or NDFD extent of the sample from the NIR data using a NIR/NDFD calibration model.

The present invention provides a method of predicting neutral detergent fiber digestibility (NDFD) properties of a feedstuff sample. The method includes developing a NIR/NDFD extent calibration model and developing a NIR/NDFD rate calibration model. Developing the calibration models includes converting gas pressure per mass of isolated NDF or whole sample from in vitro gas production of a calibration feedstuff sample to NDFD using an IVGP/NDFD correlation algorithm. Developing the calibration models includes determining NDFD rate and NDFD extent from the NDFD using an equation that relates at least NDFD, time, the NDFD rate, and the NDFD extent. Developing the calibration models includes measuring NIR data from the calibration sample. Developing the calibration models includes correlating the NIR data from the calibration sample to the NDFD rate of the calibration sample to develop the NIR/NDFD rate calibration model. Developing the calibration models also includes correlating NIR data from the calibration sample to the NDFD extent of the calibration sample to develop the NIR/NDFD extent calibration model. The method includes collecting a near-infrared spectrum of the sample to provide NIR data of the sample. The method includes predicting the NDFD extent of the sample from the NIR data using an NIR/NDFD extent calibration model. The method also includes predicting the NDFD rate of the sample from the NIR data using an NIR/NDFD rate calibration model.

The present invention provides a method of predicting digestibility of a feedstuff sample for an animal at a rumen passage rate (eNDF). The method includes collecting a near-infrared spectrum of the feedstuff sample to provide NIR data of the feedstuff sample. The method includes predicting NDFD rate of the sample from the NIR data using an NIR/NDFD rate calibration model. The method includes predicting NDFD extent of the sample from the NIR data using an NIR/NDFD extent calibration model. The method also includes predicting eNDF of the sample using an equation that relates at least the NDFD rate, the NDFD extent, the rumen passage rate, and the eNDF.

The present invention provides a method of predicting neutral detergent fiber digestibility (NDFD) properties of a feedstuff sample. The method includes determining a gas pressure per mass of isolated NDF or whole sample from in vitro gas production of the isolated NDF of the feedstuff sample or a whole sample of the feedstuff sample at one or more elapsed times. The method also includes converting the gas pressure per mass of the isolated NDF or whole sample at the elapsed time to a predicted NDFD at the elapsed time using an IVGP/NDFD correlation algorithm.

In various embodiments, the present invention provides advantages over other methods of predicting NDFD and/or NDFD kinetics (e.g., NDFD rate and/or NDFD extent) of feedstuff samples. For example, various embodiments provide prediction of NDFD, NDFD rate, and/or NDFD extent of a feedstuff sample from NIR data of the feedstuff sample, which is a more rapid, less costly, and safer technique than directly measuring NDFD such as via the Daisy Jar method or an in situ method. Various embodiments provide prediction of NDFD of a feedstuff sample from in vitro gas production (IVGP) of the NDF of the feedstuff sample, which is a more rapid, less costly, and safer technique than directly measuring NDFD of the sample. In various embodiments, in vitro gas production is correlated to NDFD which provides more rapid and lower cost NIR calibration than directly calibrating NIR to NDFD, NDFD rate, and/or NDFD extent. In various embodiments, the lower cost, greater speed, and increased safety of the methods allows for a larger number of analyses within a fixed timeframe and budget, increasing precision and accuracy of the results compared to directly measuring NDFD. In various embodiments, due to the reduced time and cost of the presently claimed methods, development of accurate and precise formulations of feeds that are tailored to nutrition needs of specific ruminants can be achieved more easily, with lower cost and shorter turnaround times.

BRIEF DESCRIPTION OF THE FIGURES

The drawings illustrate generally, by way of example, but not by way of limitation, various embodiments of the present invention.

DETAILED DESCRIPTION OF THE INVENTION

Figure 1:
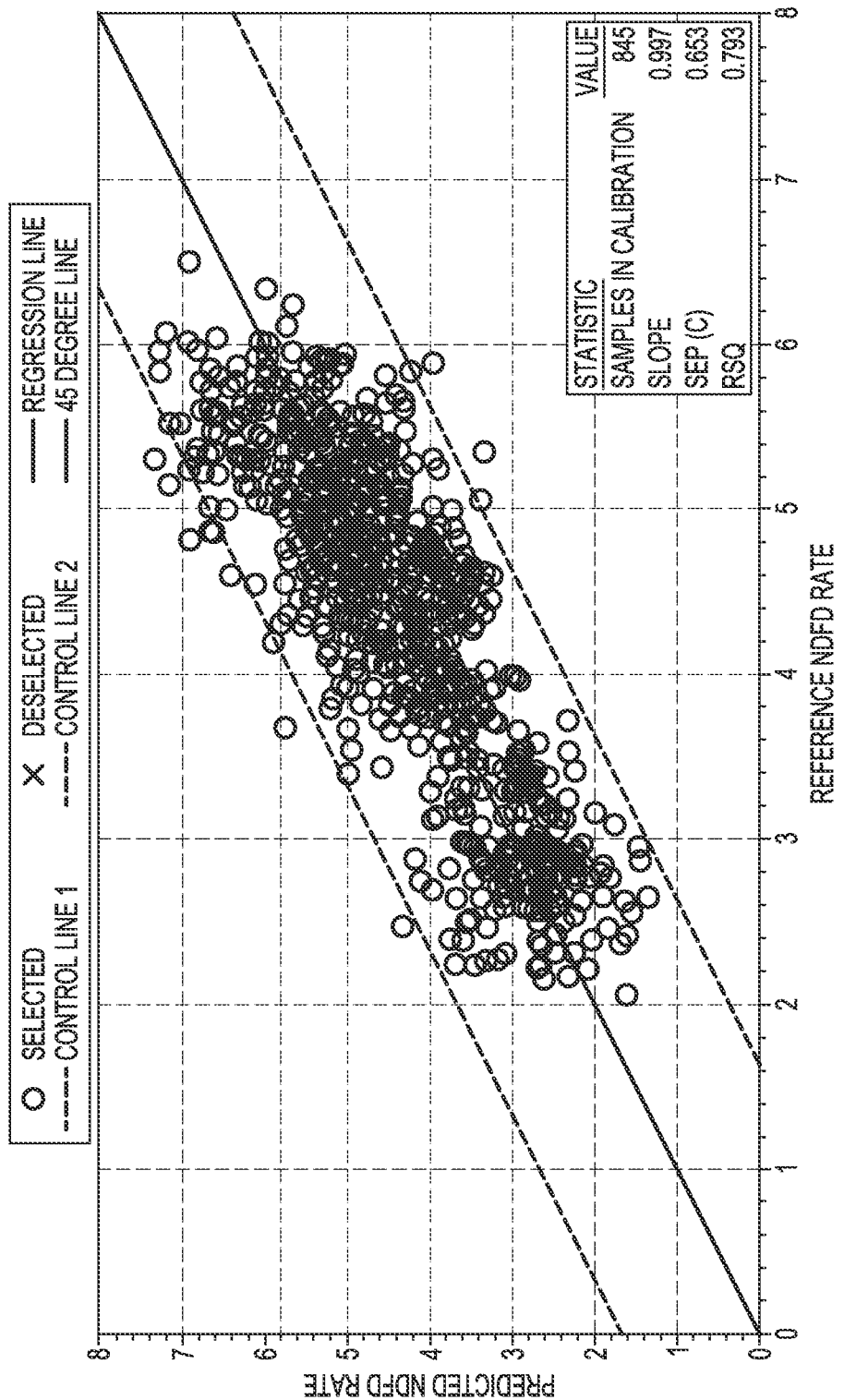
FIG. 1 illustrates a plot of predicted NDFD rate versus reference NDFD rate, in accordance with various embodiments.

Reference will now be made in detail to certain embodiments of the disclosed subject matter. While the disclosed subject matter will be described in conjunction with the enumerated claims, it will be understood that the exemplified subject matter is not intended to limit the claims to the disclosed subject matter.

Throughout this document, values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. The statement "at least one of A and B" or "at least one of A or B" has the same meaning as "A, B, or A and B." In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section.

In the methods described herein, the acts can be carried out in any order without departing from the principles of the invention, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range, and includes the exact stated value or range.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more, or 100%. The term "substantially free of" as used herein can mean having none or having a trivial amount of, such that the amount of material present does not affect the material properties of the composition including the material, such that about 0 wt % to about 5 wt % of the composition is the material, or about 0 wt % to about 1 wt %, or about 5 wt % or less, or less than, equal to, or greater than about 4.5 wt %, 4, 3.5, 3, 2.5, 2, 1.5, 1, 0.9, 0.8, 0.7, 0.6, 0.5, 0.4, 0.3, 0.2, 0.1, 0.01, or about 0.001 wt % or less, or about 0 wt %.

Method of Predicting NDFD Properties of a Feedstuff Sample Using NIR.

Various embodiments of the present invention provide a method of predicting neutral detergent fiber digestibility (NDFD) properties of a feedstuff sample. The method can include collecting a near-infrared spectrum of the feedstuff sample to provide NIR data of the feedstuff sample. The method can also include predicting NDFD of the sample at an elapsed time, NDFD rate of the sample, and/or NDFD extent of the sample from the NIR data using a NIR/NDFD calibration model (e.g., at one time, or at multiple elapsed times). The method can include predicting the NDFD without predicting the NDFD rate or the NDFD extent; predicting the NDFD rate and the NDFD extent without determining NDFD; or predicting each of the NDFD, the NDFD rate, and the NDFD extent.

The NIR/NDFD calibration model relates NIR data of a feedstuff sample to NDFD properties (e.g., NDFD, NDFD rate, and/or NDFD extent). The NIR/NDFD calibration model can include a determined correlation between NIR data and NDFD, one or more algorithms relating NIR data and NDFD, or a combination thereof.

The NIR/NDFD calibration model can include an NIR/NDFD extent calibration model and an NIR/NDFD rate calibration model. The NIR/NDFD extent calibration model can include a determined correlation between NIR data and NDFD extent, one or more algorithms relating NIR data and NDFD extent, or a combination thereof. The NIR/NDFD rate calibration model can include a determined correlation between NIR data and NDFD rate, one or more algorithms relating NIR data and NDFD rate, or a combination thereof.

Predicting the NDFD at the elapsed time from the NIR data can include predicting NDFD extent and NDFD rate from the NIR data using the NIR/NDFD calibration model, and predicting NDFD at the elapsed time using an algorithm that relates at least NDFD, time, the NDFD extent, and the NDFD rate. Any suitable algorithm that relates at least NDFD, time, the NDFD extent, and the NDFD rate can be used. For example, the algorithm can be NDFD=NDFD extent*(1−EXP(−NDFD rate*(time_hrs−NDFD lag))), as discussed in the Examples. NDFD lag can be a constant for the particular type of feedstuff sample. The method can include predicting NDFD at a time t from the NDFD rate and the NDFD with the algorithm that relates at least the NDFD rate, the NDFD extent, and the NDFD at time t. The method can include generating a table and/or chart of NDFD versus time t using the equation that relates at least the NDFD rate, the NDFD extent, and the NDFD at time t. The method can include using the table and/or chart to predict NDFD of the sample at a particular time. Predicting the NDFD at the elapsed time from the NIR data can include predicting NDFD extent from the NIR data using an NIR/NDFD extent calibration model, predicting NDFD rate from the NIR data using an NIR/NDFD rate calibration model, and predicting NDFD at the elapsed time using an algorithm that relates at least NDFD, time, the NDFD extent, and the NDFD rate.

The method can include developing the NIR/NDFD calibration model. The calibration model can be developed in any suitable way, such that the NIR/NDFD calibration model relates NIR data for the sample to NDFD of the sample. The method can include measuring NIR data from a calibration feedstuff sample and correlating the NIR data from the calibration feedstuff sample to NDFD of the calibration feedstuff sample. The method can include collecting or predicting the NDFD data of the calibration sample that is correlated to the measured NIR data. The NDFD of the sample used to develop the correlation model can be measured or predicted in any suitable way, such as via Daisy Jar method, an in vitro filtration method, an in situ method, an in vitro gas production method, or a combination thereof. The method can include collecting the NDFD of the sample, predicting the NDFD of the sample using an indirect method such as IVGP, or a combination thereof. Using the NDFD of the sample, the NDFD rate and NDFD extent can be determined using an equation that relates at least NDFD, time, the NDFD rate, and the NDFD extent, such as NDFD=NDFD extent*(1−EXP(−NDFD rate*(time_hrs−NDFD lag))). The equation can relate at least the NDFD, time, the NDFD rate, the NDFD extent, and the NDFD lag. Developing the NIR/NDFD calibration model can include developing a NIR/NDFD extent calibration model and developing a NIR/NDFD rate calibration model. The NIR/NDFD extent calibration model can correlate the NIR data and the NDFD extent. The NIR/NDFD rate calibration model can correlate the NIR data and the NDFD rate.

Predicting the NDFD of the calibration sample can include using an in vitro gas production method, including converting gas pressure per mass of isolated NDF or whole sample from in vitro gas production of the calibration sample at an elapsed time to NDFD using an IVGP/NDFD correlation algorithm. The IVGP/NDFD correlation algorithm can be any suitable algorithm that relates at least IVGP and NDFD, such as NDFD=Coef 1+(Coef 2*gas psi)+(Coef 3*(gas psi)$^2$), as discussed in the Examples. Developing the NIR/NDFD calibration model can include converting gas pressure per mass of isolated NDF or whole sample from in vitro gas production of a calibration feedstuff sample to NDFD using an IVGP/NDFD correlation algorithm, measuring NIR data from the calibration sample, and correlating the NIR data from the calibration sample to the NDFD of the calibration feedstuff sample. Developing the NIR/NDFD calibration model can include converting gas pressure per mass of isolated NDF or whole sample from in vitro gas production of a calibration feedstuff sample to NDFD using an IVGP/NDFD correlation algorithm, determining NDFD rate and NDFD extent from the NDFD using an equation that relates at least NDFD, time, the NDFD rate, and the NDFD extent, measuring NIR data from the calibration sample, correlating the NIR data from the calibration sample to the NDFD rate of the calibration sample to develop a NIR/NDFD rate calibration model, and correlating NIR data from the calibration sample to the NDFD extent of the calibration sample to develop a NIR/NDFD extent calibration model.

The method can include predicting digestibility of the feedstuff sample for an animal at a rumen passage rate (eNDF) using an algorithm that relates at least the NDFD rate, the NDFD extent, the rumen passage rate, and the eNDF. Any suitable algorithm that relates at least eNDF, the rumen passage rate, the NDFD rate, and the NDFD extent can be used. For example, the algorithm can be eNDF= (NDFD extent*NDFD rate*EXP(−passage rate*NDFD lag))/(NDFD rate+passage rate), as discussed in the Examples. The equation can relate at least eNDF, the rumen passage rate, the NDFD rate, the NDFD extent, and the NDFD lag time. The method can include generating a table and/or chart of the eNDF versus rumen passage rate using the algorithm that relates at least the NDFD rate, the NDFD extent, the rumen passage rate, and the eNDF. The method can include using the table and/or chart to predict eNDF at a rumen passage rate.

In the methods described herein, the NDFD that is predicted by the method (and/or the NDFD extent or the NDFD rate) can be any suitable NDFD, such as a Daisy Jar NDFD, an in vitro filtration NDFD, an in situ NDFD, or an in vivo NDFD. The NDFD can be an in vivo method NDFD, such as determined via total collection technique or marker technique. The predicted NDFD can be an in situ technique NDFD, such as an in sacco or nylon bag technique. The predicted NDFD can be an in vitro method NDFD, such as a measure feed NDF disappearance NDFD, a RUSITEC NDFD, a NDFD determined via batch culture in individual vessels, or a Daisy-Ankom incubator NDFD. The predicted NDFD can be an NDFD determined via measuring gas produced by the fermented feed (e.g., whole feedstuff material or isolated from the feed), such as via batch-closed systems (e.g., sealed bottle), or via batch-open systems (e.g., manual or automatic). The NDFD predicted by the method can be a Daisy Jar NDFD.

In the methods described herein, the feedstuff sample can be any suitable feedstuff sample. The feedstuff sample can include a forage sample, corn and/or corn by-products (e.g., corn gluten feed, corn gluten meal, distiller grain, wet distillers grains, corn germ, and the like), wheat and/or wheat by-product (e.g., wheat bran, wheat mids, wheat germ, and the like), soybean and soybean by-products (e.g., soybean meal, soyhulls, and the like), oats and oats by-products (e.g., oats hulls), barley and barley by-products (e.g., brewers grains, and the like), beet pulp, citrus pulp, cottonseed and cottonseed by products (e.g., cottonseed hulls, cotton burrs), sunflowers and sunflower by-products (e.g., sunflower meal, sunflower hulls), canola/rapeseed and canola/rapeseed by-products (e.g., canola/rapeseed meal), rice by-product (e.g., rice bran, and the like), peas and by-product (e.g., pea culls, and the like), rye and/or by-product (e.g., rye distiller, and the like), other by-product (e.g., peanut hulls, malt sprouts, hemp by-product, and the like), or a combination thereof.

The feedstuff sample can be a forage sample. The forage sample can be any suitable forage sample, such as brown midrib corn silage, corn silage, ensiled barley, ensiled fresh legume, ensiled fresh mix forage, ensiled fresh small grain, ensiled grass (e.g., ensiled ryegrass, canary, and/or orchard grass), ensiled fresh grass, ensiled legume (e.g., ensiled alfalfa), ensiled mix forage (e.g., ensiled forages that include mixes of legumes, grasses, small grains; e.g., ensiled alfalfa/grass mixture), ensiled small grain (e.g., ensiled rye, triticale, oats), ensiled sorghum (e.g., ensiled Sudan grass), grass hay (e.g., dry ryegrass, canary, or orchard grass), legume hay (e.g., dry alfalfa), mix forage hay (e.g., dry hay that includes mixes of legumes, grasses, small grains; e.g., dry alfalfa/grass mixed), small grain hay (e.g., dry rye, triticale, oats), or a combination thereof.

Method of Predicting Digestibility of a Feedstuff Sample for an Animal at a Rumen Passage Rate (eNDF).

In various embodiments, the present invention provides a method of predicting digestibility of a feedstuff sample for an animal at a rumen passage rate (eNDF). The method can include predicting NDFD, NDFD rate, and/or NDFD extent as described above. In some embodiments, the method can include predicting NDFD rate and NDFD extent without predicting NDFD. For example, the method can include collecting a near-infrared spectrum of the feedstuff sample to provide NIR data of the feedstuff sample. The method can include predicting NDFD rate of the sample from the NIR data using an NIR/NDFD rate calibration model. The method can include predicting NDFD extent of the sample from the NIR data using an NIR/NDFD extent calibration model. The method can also include predicting eNDF of the sample using an equation that relates at least the NDFD rate, the NDFD extent, the rumen passage rate, and the eNDF. For example, the algorithm can be eNDF=(NDFD extent*NDFD rate*EXP(−passage rate*NDFD lag))/(NDFD rate+passage rate), as discussed in the Examples.

Method of Predicting NDFD Properties of a Feedstuff Sample Using Predicted or Measured IVGP.

Various aspects of the present invention provide a method of predicting neutral detergent fiber digestibility (NDFD) properties of a feedstuff sample. The method can include determining a gas pressure per mass of isolated NDF from in vitro gas production of the isolated NDF of the feedstuff sample at one or more elapsed times, or the method can include determining a gas pressure per mass of whole sample from in vitro gas production of the whole sample of the feedstuff sample at one or more elapsed times. The method can include converting the gas pressure per mass of the isolated NDF or whole sample at the elapsed time to a predicted NDFD at the elapsed time using an IVGP/NDFD correlation algorithm. The IVGP/NDFD correlation algorithm can be any suitable algorithm that correlates IVGP and NDFD. For example, the algorithm can be NDFD=Coef 1+(Coef 2*gas psi)+(Coef 3*(gas psi)$^2$), as discussed in the Examples.

The method can include predicting NDFD, NDFD rate, and/or NDFD extent using measured IVGP. The determining of the gas pressure per mass of the isolated NDF or whole sample from in vitro gas production of the feedstuff sample can include performing the in vitro gas production and measuring the gas pressure per mass of the isolated NDF or whole sample. The method can include measuring the gas pressure per mass of the isolated NDF or whole sample from in vitro gas production at multiple elapsed times (e.g., at least two times). The method can include converting the gas pressure per mass of the isolated NDF or whole sample at two or more of the elapsed times to a predicted NDFD at the two or more elapsed times using the IVGP/NDFD correlation algorithm. The method can further include converting the gas pressure per mass of the isolated NDF or whole sample at the elapsed time to a predicted NDFD slope (e.g., the rate of change of NDFD at time t) using an IVGP/NDFD correlation algorithm. The method can include measuring the gas pressure per mass of the isolated NDF or whole sample from in vitro gas production at multiple elapsed times. The method can include converting the measured gas pressure per mass at two or more of the elapsed times to a predicted NDFD at the two or more elapsed times using the IVGP/NDFD correlation algorithm. The method can also include predicting an NDFD slope at one or more times from the NDFD at the two or more elapsed times. The method can include determining NDFD slopes at multiple times from the NDFD at two or more of the elapsed times.

The method can include predicting NDFD rate and NDFD extent from the predicted NDFD with an equation that relates at least the NDFD rate, the NDFD extent, and the NDFD at time t. The equation can be any suitable equation that relates NDFD rate, NDFD extent, NDFD, and time, such as NDFD=NDFD extent*(1−EXP(−NDFD rate*(time_hrs−NDFD lag))), as discussed in the Examples. The method can further include generating a table and/or chart of NDFD versus time t. The method can include using the table and/or chart to predict NDFD and/or NDFD rate at a particular time.

The method can include predicting digestibility of the feedstuff sample for an animal at a rumen passage rate (eNDF) using an algorithm that relates at least the NDFD rate, the NDFD extent, the rumen passage rate, and the eNDF. Any suitable algorithm that relates at least eNDF, rumen passage rate, the NDFD rate, and the NDFD extent can be used. For example, the algorithm can be eNDF=(NDFD extent*NDFD rate*EXP(−passage rate*NDFD lag))/(NDFD rate+passage rate), as discussed in the Examples. The method can include generating a table and/or chart of the eNDF using the algorithm that relates at least the NDFD rate, the NDFD extent, the rumen passage rate, and the eNDF. The method can include using the table and/or chart to predict eNDF at a particular rumen passage rate.

The in vitro gas production from the feedstuff sample can include gas pressure generated from a sealed container including a rumen fluid and isolated NDF or whole sample from the feedstuff sample. The sealed container can be heated and agitated during the in vitro gas production.

The method of predicting neutral detergent fiber digestibility (NDFD) properties of a feedstuff sample using IVGP can be a method of developing an NIR/NDFD calibration model, such as a NIR/NDFD rate calibration model and a NIR/NDFD extent calibration model. The method can be a method of developing an NIR/NDFD calibration model that correlates NDFD, NDFD rate, and/or NDFD extent with NIR data using IVGP to determine NDFD properties, and without using techniques for measuring NDFD properties that are more time-consuming than IVGP (e.g., without using the Daisy Jar method to determine NDFD).

The method of developing the NIR/NDFD calibration model can include determining NDFD rate and NDFD extent from the predicted NDFD (e.g., the NDFD predicted via IVGP) at the elapsed time using an equation that relates at least the NDFD rate, the NDFD extent, the NDFD, and time. The method can be a method of predicting NDFD properties of a feedstuff sample that includes collecting a near-infrared spectrum of the sample to provide NIR data of the sample. The method can include predicting the NDFD extent of the sample from the NIR data using the NIR/NDFD extent calibration model. The method can include predicting the NDFD rate of the sample from the NIR data using the NIR/NDFD rate calibration model. The method can also include predicting NDFD at the elapsed time using an algorithm that relates at least NDFD, time, the NDFD rate, and the NDFD extent.

Examples

Various embodiments of the present invention can be better understood by reference to the following Examples which are offered by way of illustration. The present invention is not limited to the Examples given herein.

Example Procedure.

An alfalfa hay forage sample went through the following steps to generate a forage report. The sample was first ground to process the sample to the proper particle size for NIR or the in vitro gas production procedure. An NDFD curve (% NDF digestion versus time) was then generated using MR data or in vitro gas production data using the following steps. An NIR spectrum of the sample was first taken. NDFD rate and extent were predicted from the NIR data. If the sample did not fit in the NIR model to predict rate and extent (e.g., if the sample was a spectrum outlier), then in vitro gas production of the sample was measured and converted to NDFD rate and extent and these data points were added to the NDFD curve or used to generate the NDFD curve.

Grinding

The equipment used was a Retsch Mill (Brinkman) Grinder or Cyclotech grinder or other grinders with 1 mm screen. The forage sample was pre-dried at ~60° C. in an air-forced oven for more than 16 h. Samples with large particles (greater than 10 mm) were pre-ground with a burr milk or a coffee grinder to break-up large particles. The samples were ground using the Retsch mill (or other grinders) with 1 mm screen. Before grinding, the sample was homogenized. The sample was poured into the opening on top of the grinder. The grinder was allowed to run long enough to ensure that there was no sample remaining in the center of the screening ring before removing it, to prevent contamination of the final sample with unground particles and to ensure that it is representative of the original sample poured into the grinder. The ground sample was poured into the corresponding bag or sample container.

NIR-Scanning.

The ground forage sample was scanned under the appropriate product in Mosaic. The equipment used was a Foss DS2500™ & accessories, Foss ISIscan NOVA operation software, and Foss Mosaic network software. A forage development product group or validated product was set up in DS2500 through Mosaic or NOVA if not connected to Mosaic. A large round cup was used to obtain a spectrum that was best representative of the sample. The sample was mixed thoroughly and the cup was at least half filled. It was ensured that the cup lens was fully covered by the sample with any air pockets in the sample presentation area. A lid was used to ensure consistent sample density when insufficient sample was present. The sample was placed back in the sample container after completion of the scanning.

NIR Model Development.

Correlation between in vitro gas production (IVGP) and Daisy Jar NDFD (DJ): DJ is one of the methods used for assessing NDFD. However, this procedure is time consuming (240 h) and expensive. We found there is correlation between gas production of NDF from IVGP and NDFD from DJ method. Therefore, we developed the correlation between in vitro gas production of NDF and NDFD for individual forage types. NDFD of forage samples were analyzed in IVGP, and gas production in psi/g were converted to NDFD in % NDF. Using the converted NDFD in % NDF, rate and extent of NDFD are generated for NIR calibration, validation, or report.

NIR calibration was performed using data generated from in vitro gas production to develop an NIR calibration model for predicting NDFD extent and rate. The NIR spectrum and reference values were combined to build the calibration database. The references values were IVGP gas production per mass of isolated NDF of the sample converted to NDFD in % NDF. The calibration database was imported into Chemometric software, and different algorithms and pre-processing treatments were applied to determine the best relationship between the reference values and NIR predictions. The statistics and x-y plot were reviewed to determine the best algorithm to use. Once the calibration model was completed, it was imported into Mosaic and the NIR instrument (DS2500) was able to predict measurement results when analyzing unknown samples.

NIR validation was performed to validate whether the developed NIR calibration model for predicting NDFD extent and rate worked as expected and to identify biases to apply on the NIR instrument. At least 20 samples were collected and scanned on the DS2500 that have reference values (IVGP gas production per mass of isolated NDF of the sample, converted to NDFD in % NDF). NIR spectra and reference values were combined to create a validation file. The validation file was imported into Chemometric software and predicted against calibration model. The statistics and x-y plot were reviewed to determine if the samples fit the calibration model. Biases were determined by taking the difference between the reference values and NIR predictions. Once the validation was completed, the biases were applied into Mosaic for each DS2500 instrument.

For reporting, a forage sample was scanned under the appropriate product in Mosaic. The models predicted the NDFD rate and extent from the NIR data.

In Vitro Gas Production.

The equipment used was an ANKOM Gas Production System, repeat dispenser bottle, pump, incubators, water baths, and glass bottles with a septa port. Isolated NDF samples (see, isolation of forage NDF) were placed into a 105° C. oven for at least 2 hours prior to weighing samples into bottles. Between 0.5000-0.5100 g of each sample were weighed into a 250 ml bottle, and the weights were recorded. All bottles were capped with the corresponding numbered Ankom transmitter units and placed in the shaking incubator. 4.125 L of McDougall's buffer was prepared and placed in the 5 L vented dispensing bottle. The McDougall's buffer was placed in water bath at 39° C. with a large stir bar and bubbling $CO_2$. 4.125 mL of 4% $CaCl_2$ were added once $CO_2$ had been bubbled for a short period. Solubilization was visually verified.

The rumen fluid was strained through one layer of fine cheese cloth while running $CO_2$ into the insulated collection thermos. The $CO_2$ was not bubbled into the rumen fluid; rather, it was used as a blanket of gas to cover the rumen fluid. 1375 mL of strained rumen fluid were measured out and added to the 4.125 L of McDougall's buffer. The mixture of 3:1 McDougall's buffer/rumen fluid was kept at 39° C. while dispensing the 50 mL of rumen fluid and McDougall's buffer mix into each bottle. Air in the bottles was again displaced with $CO_2$ and the bottles were recapped. Each bottle was purged and they were returned to the incubator in groups.

To purge the bottles, the program "Gas Pressure Monitor.exe" was opened in the ANKOM Gas Production System. The "Live Interval" was set to 1 second and the "Global release" was set to 8 psi. Once all bottles were purged and back in the shaking incubator, the universal release was set to 1 psi. The bottles were allowed to warm for approximately 5 minutes. The vents on all bottles were released, allowing any built-up pressure to escape, and it was verified that all bottles had returned to, or near, current pressure of 0.0 psi+/−0.14 psi. A recording interval of 15 minutes was verified and the live interval was adjusted to 1 minute (60 seconds).

The shaker was started and set at 90 rpm.

Once 48 hours of data were collected, the data was saved and the stop button was pressed. All the gas curves were reviewed, looking for outliers and bottle failures. Bottles were removed that had clear failures such as flat lines or clear raises or drops in pressure from mechanical error. It was ensured that only valid curves were used to calculate the blank average. Typical blank curves produced about 1 psi of pressure before slowly declining. At each time point recorded, the value of the psi generated from the blank was subtracted from the corresponding time point of each sample to remove the background of gas produced strictly from the rumen fluid alone. The psi value was then divided by the amount of NDF loaded in that bottle to give the units of psi/g: (recorded psi−blank psi)/g of NDF.

Isolation of Forage NDF.

The equipment used was a Soxhlet fat extraction apparatus Ankom[2000], Ankom Fiber filter bags, Acetone Resistant Marker, and Modified Ankom tray stack. Ground forage samples (1.5-2.5 g each) were weighed in Ankom Fiber filter bags and the bags were sealed. The samples were de-fatted by following a Soxhlet De-fatting Procedure: Any samples containing high amounts of chlorophyll (e.g., alfalfa type hays) were spread out as these take the greatest amount of time to properly extract; the samples were refluxed for a minimum of 90 minutes or until the pet ether remained clear; excess petroleum ether was squeezed back into the vessel and the bags were placed in a pan to dry in the hood.

The bags were loaded into the modified trays ensuring that each level was at a different rotation than the one previous. The three control F57 bags were placed on the 1$^{st}$ or bottom tier. Hot water was added to the fill line of the amylase rinse bucket. 4 mL of Termamyl or Ankom Alpha Amylase were added to the amylase rinse bucket. The sample suspender was placed into the pot and the weight was added to the top of the suspender to hold the trays and bags down. 30 g of sodium sulfite was added to the top of the stack, near the location the buffer fills the pot. NDF was selected and the extraction was started. 1 mL of Termamyl or Ankom Alpha Amylase were added to the inside of the pot and the lid was closed securely.

Once the first extraction was complete, the sample chamber was slowly opened. The bag suspender was removed and the bag was brought to the washing station. Once cool enough to touch, the bags were removed and rinsed with hot water. The bags were sorted in order and placed back in the bag holder for a second extraction. The order of bags 4-17 was reversed so that the bags that were on the bottom in the first extraction were on the top in the second extraction and they were placed in the opposite vertical orientation as well. The second extraction was performed similarly to the first extraction.

After completion of the second extraction, including rinsing the bags a second time, the bags were placed in a drying oven at 100-105° C. for overnight drying. The bags were removed from the oven and allowed to cool to room temperature in a desiccator. The bags were weighed and the weights recorded. The sample was removed from the bag and placed in a small coffee grinder and ground until it reached a powder-like consistency. Once ground, it was collected in a pre-labeled aluminum dish and set in the metal tray for later drying. Compressed air was used to clean the coffee grinder between samples. Any visible residues were wiped with a Kimwipe before starting the next sample. It was ensured that a sufficient amount of NDF had been extracted for the desired purpose. If samples were not used right away, the metal drying tray and samples were covered with a single layer of cheese cloth to prevent agitation or contamination of the samples prior to drying.

Daisy Jar Method.

The equipment used was a Daisy Jar Incubator, 4 Daisy jars with one-way venting lids and agitation inserts, Ankom F57 bags. The weight of all F57 bags was first recorded. Then each bag was filled with 0.5 g+/−0.015 g of the ground forage sample and these weights were recorded as well. The F57 bags were sealed and the sample was distributed evenly across the bag. The buffers described in Tables 1 and 2 were prepared. For a standard run of 4 Daisy jars, 6 L of Buffer A and 1.5 L of Buffer B were prepared. Buffers A and B, the Daisy jars, and all the other materials needed were heated in an incubator overnight at 39° C.

TABLE 1

| Buffers A. Amounts listed are per 6 L. | |
| --- | --- |
| $KH_2PO_4$ | 60 g |
| $MgSO_4\ 7H_2O$ | 3 g |
| NaCl | 3 g |
| $CaCl_2\ 2H_2O$ | 0.6 g |
| Urea | 3 g |

For preparation of Buffer A, 2.5-3 L of distilled $H_2O$ and the reagents were added to a large beaker in the order shown in Table 1. Once all components were completely dissolved, a graduated cylinder was used to measure up to a total volume of 6 L with distilled $H_2O$. The 6 L was added to a 10 L carboy, and the opening was covered with a cap to prevent evaporation.

TABLE 2

| Buffer B. Amounts given are per 1.5 L. | |
| --- | --- |
| $Na_2CO_3$ | 22.5 g |
| $Na_2S\ 9H_2O$ | 1.5 g |

For preparation of Buffer B, 800 mL of distilled $H_2O$ was added to a large beaker. The components were added in the order shown in Table 2. Once completely dissolved, the total volume was raised to 1.5 L with distilled $H_2O$. The 1.5 L was placed in a 2 L container with a lid until needed.

1.5 L of Buffer B was added to the 10 L carboy containing the 6 L of Buffer A. The buffer pH was between 6.75-6.85. The F57 bags were distributed into their appropriate jars. Even and odd numbered bags were placed across either side of the jar divider to separate replicates. 1.6 L of the combined buffers were added to each jar. The lids of the jars were tightly secured and the jars were placed in the Daisy incubator to begin incubation and rotation. The bags were soaked this way for at least 15 minutes but not longer than 1 hour before rumen fluid was added.

The rumen fluid pH was measured and recorded prior to straining. The rumen fluid was strained through one layer of fine cheese cloth while running $CO_2$ into the collection insulated thermos. The $CO_2$ was not bubbled in the rumen fluid; rather, it was used as a blanket of gas to cover the rumen fluid. The strained rumen fluid was mixed in the thermos and 400 mL of strained rumen fluid was measured out in a graduated cylinder and added to the first jar. The jar was purged with $CO_2$ and returned to the Daisy incubator. The process was repeated for the remaining 3 jars. The time of returning the jars to the incubator was recorded, and the jars were monitored until their collection time.

At the collection time, the jars were emptied and the bags were collected and rinsed briefly with distilled water. The bags were gently pressed as they were stacked together to remove most of the water. The bags were either directly placed in an oven to dry overnight at 60° C., or first refrigerated at 4° C. until ready to dry in the oven. Once dried, the bags were distributed in groups of 21 bags with NDF extraction controls and were prepared for ANKOM NDF extraction. Once NDF extraction was complete, the weights were recorded. The amount of NDF degraded in each bag was calculated as % NDF=(g NDF recovered/g NDF in starting material)×100.

Correlation Between In Vitro Gas Production and Daisy Jar Method.

The data generated by the Daisy and in vitro gas production was used to develop mathematical models to correlate NDFD with GP for 16 forage types (BMR: Brown midrib corn silage; CS: Corn silage; EHB: Ensiled barley; EHFL: Ensiled fresh legume; EHFM: Ensiled fresh mix forage; EHFSG: Ensiled fresh small grain; EHFG: Ensiled fresh grass; EHG: Ensiled grass; e.g., Ensiled Ryegrass, Canary and Orchard grass; EHL: Ensiled legume; e.g., Ensiled Alfalfa; EHM: Ensiled Forages that contain mixes of Legumes, Grasses, Small Grains, e.g., Ensiled Alfalfa/grass mixed; EHSG: Ensiled small grain, e.g., Ensiled Rye, Triticale, Oats; EHSS: ensiled sorghum, e.g., Ensiled Sudan grass; HG: Grass hay, e.g., Dry Ryegrass, Canary and Orchard grass; HL: Legume hay, e.g., Dry Alfalfa; HM: Dry Hay that contain mixes of Legumes, Grasses, Small Grains, e.g., Dry Alfalfa/grass mixed; HSG: small grain hay, e.g., Dry Rye, Triticale, Oats). The developed equations allowed conversion of gas produced in psi/g of NDF into NDFD for each sample at the selected time points and/or determination of the lag, rate, and/or extent of NDF digestion. The equation used to convert gas produced from the in vitro gas production to Daisy NDFD in % NDF was NDFD=Coef 1+(Coef 2*gas psi)+(Coef 3*(gas psi)$^2$). The values of the coefficients are given in Table 3, which are specific for each forage type. The same dataset of Daisy NDFD was used to generate a curve of NDFD by time for each forage type. The lag times (shown in Table 4) were determined and set as constant when calculating NDFD of different timepoints in step "NDFD Curve Generation".

TABLE 3

Coefficients 1-3 for various forage types.

| Forage type | Coef 1 | Coef 2 | Coef 3 |
|---|---|---|---|
| CS | 6.33855 | 2.03018 | 0.04853 |
| BMR | 4.97528 | 1.49740 | 0.08061 |
| HL | 11.02829 | 5.49691 | -0.17693 |
| EHL | 10.29790 | 4.47171 | -0.04131 |
| EHG | 10.15893 | 4.97967 | -0.09277 |
| EHM | 12.24170 | 5.83163 | -0.15226 |
| EHSG | 8.73787 | 4.93830 | -0.11271 |
| EHSS | 5.86129 | 4.14628 | -0.07115 |
| HG | 8.55508 | 4.06278 | -0.06061 |
| EHB | 12.25661 | 2.38862 | 0.01225 |
| EHFM | 12.10828 | 4.74565 | -0.09379 |
| EHFSG | 13.35126 | 4.94779 | -0.10588 |
| HM | 12.62248 | 4.78184 | -0.12376 |
| HSG | 5.88397 | 4.22873 | -0.08712 |
| EHFG | 13.88447 | 4.28458 | -0.05166 |
| EHFL | 10.82945 | 4.72483 | -0.11601 |

TABLE 4

Lag times for various forage types.

| Forage type | Lag time |
|---|---|
| BMR | 4 |
| CS | 3 |
| EHB | 0.2 |
| EHFG | 1 |
| EHFL | 4 |
| EHFM | 3 |
| EHFSG | 2.7 |
| EHG | 3 |
| EHL | 3.1 |
| EHM | 4 |
| EHSG | 4 |
| EHSS | 4 |
| HG | 4 |
| HL | 2.6 |
| HM | 1.3 |
| HSG | 4 |

IVGP obtains a more rapid result than Daisy Jar NDFD, and the times of the "gas psi" in the equation NDFD=Coef 1+(Coef 2*gas psi)+(Coef 3*(gas psi)$^2$) are not the same as Daisy Jar NDFD times. Table 5 illustrates Daisy NDFD times versus IVGP times.

TABLE 5

Daisy NDFD times versus IVGP times.

| Daisy Jar time (h) | IVGP time (h) |
|---|---|
| 6 | 1 |
| 12 | 6 |
| 30 | 14 |
| 48 | 20 |
| 120 | 36 |
| 240 | 48 |

NDFD Curve Generation.

To generate a curve of NDFD (% NDF) versus time, once a sample had an NDFD rate and NDFD extent as determined from NIR model or in vitro gas production, it was combined with the NDFD lag time for that forage type (Table 4), and input into the following equation to generate the digestibility curve: NDFD at time t=NDFD extent*(1-EXP(-NDFD rate*(time_hrs-NDFD lag))). The standard timepoints of 48, 72, 120, and 240 h were predicted and inserted for the specific sample. If the calculated NDFD value is below zero, it is defaulted to zero.

To predict final digestibility of a forage specific to an animal (effective NDFD, or eNDF), the NDFD rate and NDFD extent for the specific forage and the specific lag times for that forage type were used. The animal factors included parameters such as body weight, physiological state, and the like. This helped determine passage rate of forage through the rumen. The passage rate and the forage digestibility curve allowed for prediction of effective digestibility. The equation used to determine eNDF was eNDF=(NDFD extent*NDFD rate*EXP(-passage rate*NDFD lag))/(NDFD rate+passage rate).

Figure 2:
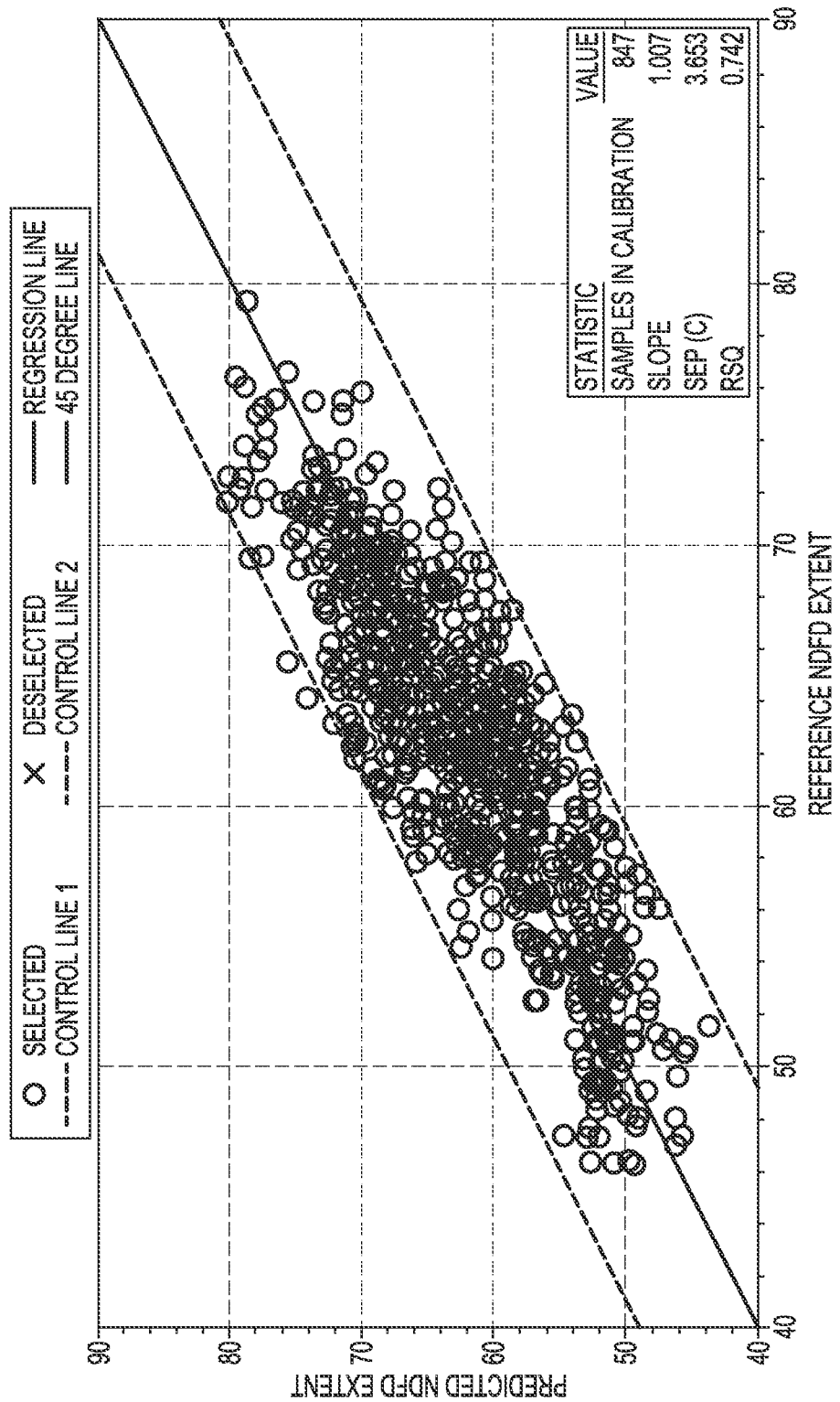
FIG. 2 illustrates a plot of predicted NDFD extent versus reference NDFD extent, in accordance with various embodiments.
Figure 3A:
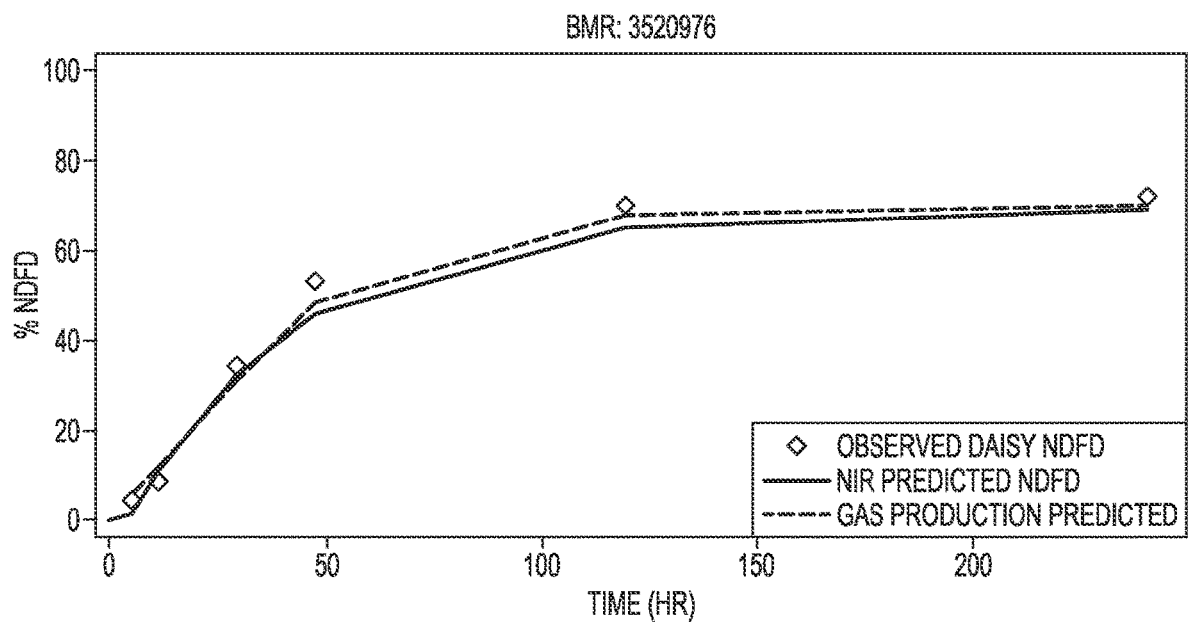
FIGS. 3A-D illustrate plots of NDFD in % NDF versus time as determined via Daisy Jar method, as predicted from IVGP technique using IVGP/NDFD correlation, and as predicted from NIR data using a NIR/NDFD rate correlation model and a NIR/NDFD extent correlation model, in accordance with various embodiments.
Figure 3B:
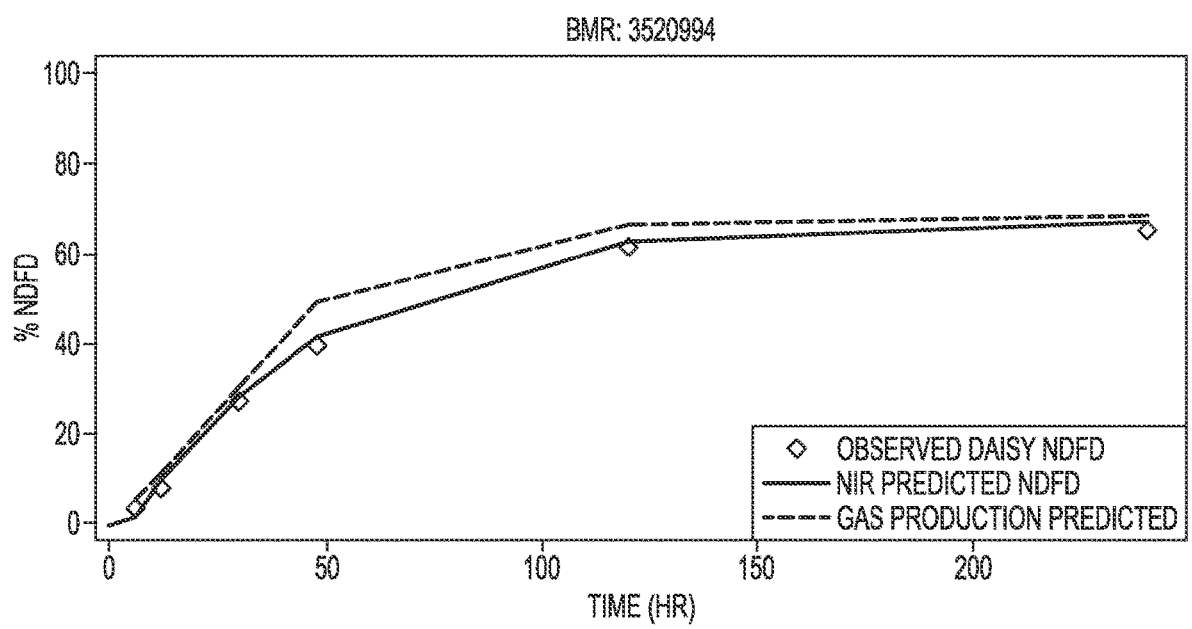
Figure 3C:
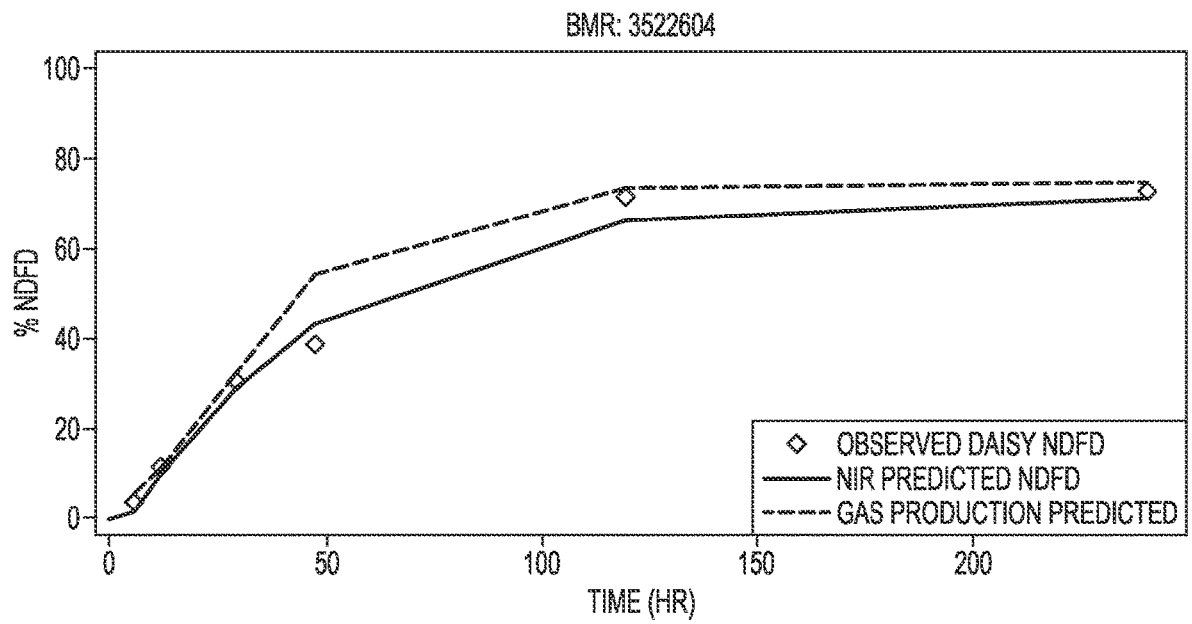
Figure 3D:
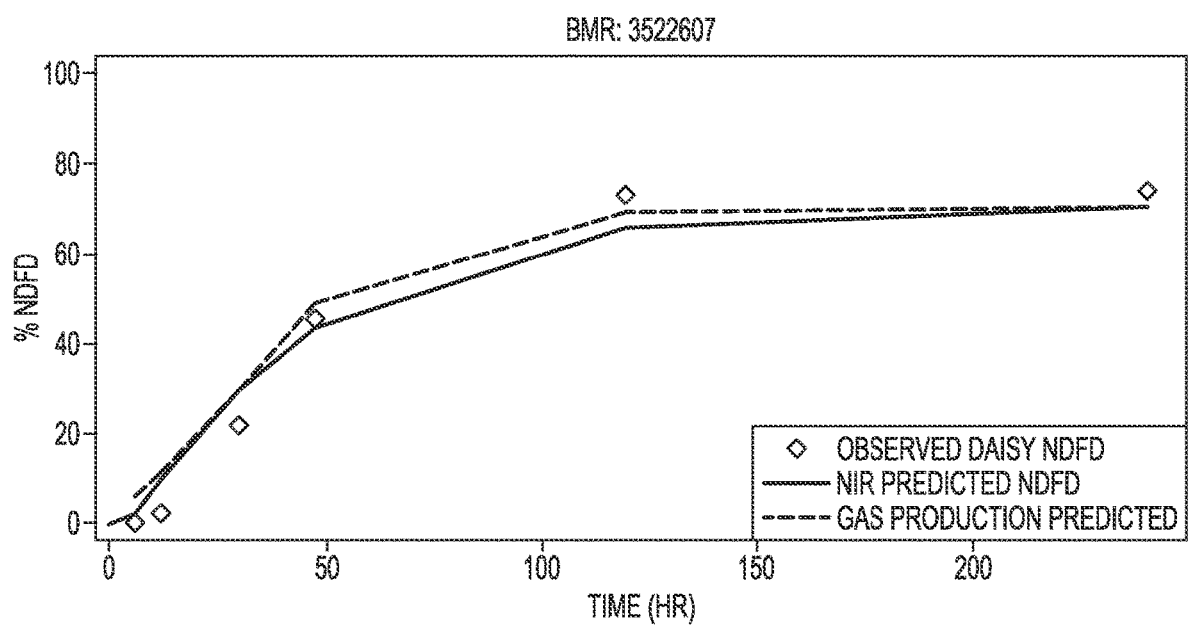

FIG. 1 illustrates a plot of predicted NDFD rate versus reference NDFD rate for all 16 forage types indicated in Table 4. FIG. 2 illustrates a plot of predicted NDFD extent versus reference NDFD extent for all 16 forage types indicated in Table 4. The reference NDFD rates and extents were determined via IVGP and converted to NDFD using the IVGP/NDFD correlation, and the predicted NDFD rates and extents were predicted via a NIR/NDFD rate correlation model and a NIR/NDFD extent correlation model developed using the method described in the Examples, with the NIR/NDFD rate and NIR/NDFD extent correlation models developed using IVGP.

FIGS. 3A-D illustrate plots of NDFD in % NDF versus time as determined via Daisy Jar method, as predicted from IVGP technique using IVGP/NDFD correlation, and as predicted from NIR data using a NIR/NDFD rate correlation model and a NIR/NDFD extent correlation model. The sample of FIG. 3A-3D was brown midrib corn silage.

The terms and expressions that have been employed are used as terms of description and not of limitation, and there is no intention in the use of such terms and expressions of excluding any equivalents of the features shown and described or portions thereof, but it is recognized that various modifications are possible within the scope of the embodiments of the present invention. Thus, it should be understood that although the present invention has been specifically disclosed by specific embodiments and optional features, modification and variation of the concepts herein disclosed may be resorted to by those of ordinary skill in the art, and that such modifications and variations are considered to be within the scope of embodiments of the present invention.

Exemplary Embodiments

The following exemplary embodiments are provided, the numbering of which is not to be construed as designating levels of importance:

Embodiment 1 provides a method of predicting neutral detergent fiber digestibility (NDFD) properties of a feedstuff sample, the method comprising:
collecting a near-infrared spectrum of the feedstuff sample to provide NIR data of the feedstuff sample; and
predicting NDFD of the sample at an elapsed time, NDFD rate of the sample, and/or NDFD extent of the sample from the NIR data using a NIR/NDFD calibration model.

Embodiment 2 provides the method of Embodiment 1, wherein the NDFD is a Daisy Jar NDFD, an in vitro filtration NDFD, an in situ NDFD, or an in vivo NDFD.

Embodiment 3 provides the method of any one of Embodiments 1-2, wherein the NDFD is a Daisy Jar NDFD.

Embodiment 4 provides the method of any one of Embodiments 1-3, wherein the feedstuff sample is a forage sample.

Embodiment 5 provides the method of any one of Embodiments 1-4, further comprising predicting the NDFD at multiple elapsed times from the NIR data using the NIR/NDFD calibration model.

Embodiment 6 provides the method of any one of Embodiments 1-5, wherein the NIR/NDFD calibration model comprises a determined correlation between NIR data and NDFD, one or more algorithms relating NIR data and NDFD, or a combination thereof.

Embodiment 7 provides the method of any one of Embodiments 1-6, wherein the NIR/NDFD calibration model comprises an NIR/NDFD extent calibration model and an NIR/NDFD rate calibration model.

Embodiment 8 provides the method of Embodiment 7, wherein the NIR/NDFD extent calibration model comprises a determined correlation between NIR data and NDFD extent, one or more algorithms relating NIR data and NDFD extent, or a combination thereof.

Embodiment 9 provides the method of any one of Embodiments 7-8, wherein the NIR/NDFD rate calibration model comprises a determined correlation between NIR data and NDFD rate, one or more algorithms relating NIR data and NDFD rate, or a combination thereof.

Embodiment 10 provides the method of any one of Embodiments 1-9, wherein predicting the NDFD at the elapsed time from the NIR data comprises predicting NDFD extent and NDFD rate from the NIR data using the NIR/NDFD calibration model, and predicting NDFD at the elapsed time using an algorithm that relates at least NDFD, time, the NDFD extent, and the NDFD rate.

Embodiment 11 provides the method of Embodiment 10, further comprising predicting NDFD at a time t from the NDFD rate and the NDFD with an equation that relates at least the NDFD rate, the NDFD extent, and the NDFD at time t.

Embodiment 12 provides the method of any one of Embodiments 10-11, further comprising predicting digestibility of the feedstuff sample for an animal at a rumen passage rate (eNDF) using an equation that relates at least the NDFD rate, the NDFD extent, the rumen passage rate, and the eNDF.

Embodiment 13 provides the method of Embodiment 12, further comprising generating a table and/or chart of the eNDF using an equation that relates at least the NDFD rate, the NDFD extent, the rumen passage rate, and the eNDF.

Embodiment 14 provides the method of Embodiment 13, further comprising using the table and/or chart to predict eNDF at a particular rumen passage rate.

Embodiment 15 provide the method of any one of Embodiments 10-14, further comprising generating a table and/or chart of NDFD versus time t using the equation that relates at least the NDFD rate, the NDFD extent, and the NDFD at time t.

Embodiment 16 provides the method of Embodiment 15, further comprising using the table and/or chart to predict NDFD of the sample at a particular time.

Embodiment 17 provides the method of any one of Embodiments 1-16 wherein predicting the NDFD at the elapsed time from the NIR data comprises predicting NDFD extent from the NIR data using an NIR/NDFD extent calibration model, predicting NDFD rate from the NIR data using an NIR/NDFD rate calibration model, and predicting NDFD at the elapsed time using an algorithm that relates at least NDFD, time, the NDFD extent, and the NDFD rate.

Embodiment 18 provides the method of any one of Embodiments 1-17, further comprising developing the NIR/NDFD calibration model.

Embodiment 19 provides the method of Embodiment 18, wherein developing the NIR/NDFD calibration model comprises developing a NIR/NDFD extent calibration model and developing a NIR/NDFD rate calibration model.

Embodiment 20 provides the method of any one of Embodiments 18-19 wherein developing the NIR/NDFD calibration model comprises measuring NIR data from a calibration feedstuff sample and correlating the NIR data from the calibration feedstuff sample to NDFD of the calibration feedstuff sample.

Embodiment 21 provides the method of Embodiment 20, further comprising collecting the NDFD data of the calibration sample that is correlated to the measured NIR data.

Embodiment 22 provides the method of Embodiment 21, wherein collecting the NDFD data of the calibration sample comprises predicting NDFD of the calibration sample.

Embodiment 23 provides the method of Embodiment 22, wherein predicting the NDFD of the calibration sample comprises converting gas pressure per mass of isolated NDF or whole sample from in vitro gas production of the calibration sample at an elapsed time to NDFD using an IVGP/NDFD correlation algorithm.

Embodiment 24 provides the method of any one of Embodiments 18-23, wherein developing the NIR/NDFD calibration model comprises converting gas pressure per mass of isolated NDF or whole sample from in vitro gas production of a calibration feedstuff sample to NDFD using an IVGP/NDFD correlation algorithm, measuring NIR data from the calibration sample, and correlating the NIR data from the calibration sample to the NDFD of the calibration feedstuff sample.

Embodiment 25 provides the method of any one of Embodiments 18-24, wherein developing the NIR/NDFD calibration model comprises converting gas pressure per mass of isolated NDF or whole sample from in vitro gas production of a calibration feedstuff sample to NDFD using an IVGP/NDFD correlation algorithm, determining NDFD rate and NDFD extent from the NDFD using an equation that relates at least NDFD, time, the NDFD rate, and the NDFD extent, measuring NIR data from the calibration sample, correlating the NIR data from the calibration sample to the NDFD rate of the calibration sample to develop a NIR/NDFD rate calibration model, and correlating NIR data from the calibration sample to the NDFD extent of the calibration sample to develop a NIR/NDFD extent calibration model.

Embodiment 26 provides a method of predicting neutral detergent fiber digestibility (NDFD) properties of a feedstuff sample, the method comprising:
developing a NIR/NDFD extent calibration model and developing a NIR/NDFD rate calibration model, comprising
converting gas pressure per mass of isolated NDF or whole sample from in vitro gas production of a calibration feedstuff sample to NDFD using an IVGP/NDFD correlation algorithm,
determining NDFD rate and NDFD extent from the NDFD using an equation that relates at least NDFD, time, the NDFD rate, and the NDFD extent,
measuring NIR data from the calibration sample,
correlating the NIR data from the calibration sample to the NDFD rate of the calibration sample to develop the NIR/NDFD rate calibration model, and
correlating NIR data from the calibration sample to the NDFD extent of the calibration sample to develop the NIR/NDFD extent calibration model;
collecting a near-infrared spectrum of the sample to provide NIR data of the sample;
predicting the NDFD extent of the sample from the NIR data using an NIR/NDFD extent calibration model; and
predicting the NDFD rate of the sample from the NIR data using an NIR/NDFD rate calibration model.

Embodiment 27 provides a method of predicting digestibility of a feedstuff sample for an animal at a rumen passage rate (eNDF) comprising:
collecting a near-infrared spectrum of the feedstuff sample to provide NIR data of the feedstuff sample;
predicting NDFD rate of the sample from the NIR data using an NIR/NDFD rate calibration model;
predicting NDFD extent of the sample from the NIR data using an NIR/NDFD extent calibration model; and
predicting eNDF of the sample using an equation that relates at least the NDFD rate, the NDFD extent, the rumen passage rate, and the eNDF.

Embodiment 28 provides a method of predicting neutral detergent fiber digestibility (NDFD) properties of a feedstuff sample, the method comprising:
determining a gas pressure per mass of isolated NDF or whole sample from in vitro gas production of the isolated NDF or whole sample of the feedstuff sample at one or more elapsed times; and
converting the gas pressure per mass of the isolated NDF or whole sample at the elapsed time to a predicted NDFD at the elapsed time using an IVGP/NDFD correlation algorithm.

Embodiment 29 provides the method of Embodiment 28, wherein the determining of the gas pressure per mass of the isolated NDF or whole sample from in vitro gas production of the feedstuff sample comprises performing the in vitro gas production and measuring the gas pressure per mass of the isolated NDF or whole sample.

Embodiment 30 provides the method of any one of Embodiments 28-29, further comprising
measuring the gas pressure per mass of the isolated NDF or whole sample from in vitro gas production at multiple elapsed times; and
converting the gas pressure per mass of the isolated NDF or whole sample at two or more of the elapsed times to a predicted NDFD at the two or more elapsed times using the IVGP/NDFD correlation algorithm.

Embodiment 31 provides the method of any one of Embodiments 28-30, further comprising converting the gas pressure per mass of the isolated NDF or whole sample at the elapsed time to a predicted NDFD slope using an IVGP/NDFD correlation algorithm.

Embodiment 32 provides the method of Embodiment 31, further comprising
measuring the gas pressure per mass of the isolated NDF or whole sample from in vitro gas production at multiple elapsed times;
converting the measured gas pressure per mass at two or more of the elapsed times to a predicted NDFD at the two or more elapsed times using the IVGP/NDFD correlation algorithm; and
predicting an NDFD slope at one or more times from the NDFD at the two or more elapsed times.

Embodiment 33 provides the method of Embodiment 32, further comprising determining NDFD slopes at multiple times from the NDFD at two or more of the elapsed times.

Embodiment 34 provides the method of any one of Embodiments 30-33, further comprising predicting NDFD rate and NDFD extent from the predicted NDFD with an equation that relates at least the NDFD rate, the NDFD extent, and the NDFD at time t.

Embodiment 35 provides the method of any one of Embodiments 30-34, further comprising generating a table and/or chart of NDFD versus time t.

Embodiment 36 provides the method of Embodiment 35, further comprising using the table and/or chart to predict NDFD and/or NDFD rate at a particular time.

Embodiment 37 provides the method of any one of Embodiments 34-36, further comprising predicting digestibility of the feedstuff sample for an animal at a rumen passage rate (eNDF) using an equation that relates at least the NDFD rate, the NDFD extent, the rumen passage rate, and the eNDF.

Embodiment 38 provides the method of any one of Embodiments 34-37, further comprising generating a table and/or chart of the eNDF versus rumen passage rate using an equation that relates at least the NDFD rate, the NDFD extent, the rumen passage rate, and the eNDF.

Embodiment 39 provides the method of Embodiment 38, further comprising using the table and/or chart to predict eNDF at a particular rumen passage rate.

Embodiment 40 provides the method of any one of Embodiments 30-39, wherein the NDFD is a Daisy Jar NDFD, an in vitro filtration NDFD, an in situ NDFD, or an in vivo NDFD.

Embodiment 41 provides the method of any one of Embodiments 30-40, wherein the NDFD is a Daisy Jar NDFD.

Embodiment 42 provides the method of any one of Embodiments 30-41, wherein the feedstuff sample is a forage sample.

Embodiment 43 provides the method of Embodiment 42, wherein the forage sample comprises brown midrib corn silage, corn silage, ensiled barley, ensiled fresh legume, ensiled fresh mix forage, ensiled fresh small grain, ensiled grass, ensiled legume, ensiled mix forage, ensiled small grain, ensiled sorghum, grass hay, legume hay, mix forage hay, small grain hay, or a combination thereof.

Embodiment 44 provides the method of any one of Embodiments 30-43, wherein the in vitro gas production from the forage sample comprises gas pressure generated from a sealed container comprising a rumen fluid and isolated NDF or whole sample from the forage sample.

Embodiment 45 provides the method of Embodiment 44, wherein the sealed container is heated and agitated during the in vitro gas production.

Embodiment 46 provides the method of any one of Embodiments 30-45, wherein the method is a method of developing an NIR/NDFD calibration model.

Embodiment 47 provides the method of Embodiment 46, wherein the method is a method of developing an NIR/NDFD extent calibration model and a NIR/NDFD rate calibration model.

Embodiment 48 provides the method of Embodiment 47, further comprising determining NDFD rate and NDFD extent from the predicted NDFD at the elapsed time using an equation that relates at least the NDFD rate, the NDFD extent, the NDFD, and time.

Embodiment 49 provides the method of Embodiment 47, wherein the method is a method of predicting NDFD properties of a feedstuff sample, the method further comprising:
collecting a near-infrared spectrum of the sample to provide NIR data of the sample;
predicting the NDFD extent of the sample from the NIR data using the NIR/NDFD extent calibration model;
predicting the NDFD rate of the sample from the NIR data using the NIR/NDFD rate calibration model; and
predicting NDFD at the elapsed time using an algorithm that relates at least NDFD, time, the NDFD rate, and the NDFD extent.

Embodiment 50 provides the method of any one or any combination of Embodiments 1-49 optionally configured such that all elements or options recited are available to use or select from.

The invention claimed is:

1. A method of predicting neutral detergent fiber digestibility (NDFD) properties of a feedstuff sample, the method comprising:
collecting a near-infrared spectrum of the feedstuff sample to provide NIR data of the feedstuff sample; and
predicting NDFD of the sample at an elapsed time, NDFD rate of the sample, and/or NDFD extent of the sample from the NIR data using a NIR/NDFD calibration model.

2. The method of claim 1, wherein the NDFD is a Daisy Jar NDFD, an in vitro filtration NDFD, an in situ NDFD, or an in vivo NDFD.

3. The method of claim 1, wherein the NDFD is a Daisy Jar NDFD.

4. The method of claim 1, wherein the feedstuff sample is a forage sample.

5. The method of claim 1, wherein the in vitro gas production from the forage sample comprises gas pressure generated from a sealed container comprising a rumen fluid and isolated NDF or whole sample from the forage sample, wherein the sealed container is heated and agitated during the in vitro gas production.

6. The method of claim 1, wherein the NIR/NDFD calibration model comprises an NIR/NDFD extent calibration model and an NIR/NDFD rate calibration model.

7. The method of claim 1, wherein predicting the NDFD at the elapsed time from the NIR data comprises predicting NDFD extent and NDFD rate from the NIR data using the NIR/NDFD calibration model, and predicting NDFD at the elapsed time using an algorithm that relates at least NDFD, time, the NDFD extent, and the NDFD rate.

8. The method of claim 7, further comprising predicting digestibility of the feedstuff sample for an animal at a rumen passage rate (eNDF) using an equation that relates at least the NDFD rate, the NDFD extent, the rumen passage rate, and the eNDF.

9. The method of claim 1 wherein predicting the NDFD at the elapsed time from the NIR data comprises predicting NDFD extent from the NIR data using an NIR/NDFD extent calibration model, predicting NDFD rate from the NIR data using an NIR/NDFD rate calibration model, and predicting NDFD at the elapsed time using an algorithm that relates at least NDFD, time, the NDFD extent, and the NDFD rate.

10. The method of claim 1, further comprising developing the NIR/NDFD calibration model.

11. The method of claim 10, wherein developing the NIR/NDFD calibration model comprises developing a NIR/NDFD extent calibration model and developing a NIR/NDFD rate calibration model.

12. The method of claim 10 wherein developing the NIR/NDFD calibration model comprises measuring NIR data from a calibration feedstuff sample and correlating the NIR data from the calibration feedstuff sample to NDFD of the calibration feedstuff sample.

13. The method of claim 12, further comprising predicting the NDFD data of the calibration sample that is correlated to the measured NIR data, wherein predicting the NDFD of the calibration sample comprises converting gas pressure per mass of isolated NDF or whole sample from in vitro gas production of the calibration sample at an elapsed time to NDFD using an IVGP/NDFD correlation algorithm.

14. The method of claim 10, wherein developing the NIR/NDFD calibration model comprises converting gas pressure per mass of isolated NDF or whole sample from in vitro gas production of a calibration feedstuff sample to NDFD using an IVGP/NDFD correlation algorithm, determining NDFD rate and NDFD extent from the NDFD using an equation that relates at least NDFD, time, the NDFD rate, and the NDFD extent, measuring NIR data from the calibration sample, correlating the NIR data from the calibration sample to the NDFD rate of the calibration sample to develop a NIR/NDFD rate calibration model, and correlating NIR data from the calibration sample to the NDFD extent of the calibration sample to develop a NIR/NDFD extent calibration model.

15. A method of predicting digestibility of a feedstuff sample for an animal at a rumen passage rate (eNDF) comprising:

collecting a near-infrared spectrum of the feedstuff sample to provide NIR data of the feedstuff sample;
predicting NDFD rate of the sample from the NIR data using an NIR/NDFD rate calibration model;
predicting NDFD extent of the sample from the NIR data using an NIR/NDFD extent calibration model; and
predicting eNDF of the sample using an equation that relates at least the NDFD rate, the NDFD extent, the rumen passage rate, and the eNDF.

16. A method of predicting neutral detergent fiber digestibility (NDFD) properties of a feedstuff sample, the method comprising:
determining a gas pressure per mass of isolated NDF or whole sample from in vitro gas production of the isolated NDF or whole sample of the feedstuff sample at one or more elapsed times; and
converting the gas pressure per mass of the isolated NDF or the whole sample at the elapsed time to a predicted NDFD at the elapsed time using an IVGP/NDFD correlation algorithm.

17. The method of claim 16, wherein the determining of the gas pressure per mass of the isolated NDF or whole sample from in vitro gas production of the feedstuff sample comprises performing the in vitro gas production and measuring the gas pressure per mass of the isolated NDF or whole sample.

18. The method of claim 16, further comprising predicting NDFD rate and NDFD extent from the predicted NDFD with an equation that relates at least the NDFD rate, the NDFD extent, and the NDFD at time t.

19. The method of claim 18, further comprising predicting digestibility of the feedstuff sample for an animal at a rumen passage rate (eNDF) using an equation that relates at least the NDFD rate, the NDFD extent, the rumen passage rate, and the eNDF.

20. The method of claim 16, wherein the method is a method of developing an NIR/NDFD calibration model.

* * * * *

UNITED STATES PATENT AND TRADEMARK OFFICE
CERTIFICATE OF CORRECTION

| | |
|---|---|
| PATENT NO. | : 11,802,834 B2 |
| APPLICATION NO. | : 17/452520 |
| DATED | : October 31, 2023 |
| INVENTOR(S) | : Kelly Curran Koski et al. |

It is certified that error appears in the above-identified patent and that said Letters Patent is hereby corrected as shown below:

In the Specification

In Column 9, Line 7, delete "MR" and insert -- NIR --, therefor.

Signed and Sealed this
Twenty-sixth Day of December, 2023

*Katherine Kelly Vidal*

Katherine Kelly Vidal
*Director of the United States Patent and Trademark Office*